United States Patent [19]

Messersmith

[11] 4,027,034
[45] May 31, 1977

[54] METHOD OF COMBATTING SWINE DYSENTERY

[75] Inventor: Robert Earl Messersmith, Lawrenceville, N.J.

[73] Assignee: Hoffmann-La Roche Inc., Nutley, N.J.

[22] Filed: Feb. 24, 1976

[21] Appl. No.: 660,894

Related U.S. Application Data

[63] Continuation-in-part of Ser. No. 471,372, May 20, 1974, Pat. No. 3,947,586.

[52] U.S. Cl. .............................................. 424/283
[51] Int. Cl.² ...................................... A61K 31/35
[58] Field of Search .................................... 424/283

[56] References Cited
OTHER PUBLICATIONS

Chem. Abst.–Chem. Substance Index, vol. 81 July–Dec. 1974, p. 2571cs.

*Primary Examiner*—Sam Rosen
*Attorney, Agent, or Firm*—Samuel L. Welt; Bernard S. Leon; Gerald S. Rosen

[57] ABSTRACT

The use of monensin and its pharmaceutically acceptable salts and esters in the oral control and prevention of swine dysentery is described.

5 Claims, No Drawings

METHOD OF COMBATTING SWINE DYSENTERY

RELATED PATENT APPLICATIONS

This application is a continuation-in-part of U.S. patent application Ser. No. 471,372, filed May 20, 1974 by Robert Messersmith, now U.S. Pat. No. 3,947,586. The benefit of the priority date of said application is hereby claimed.

DETAILED DESCRIPTION OF THE INVENTION

This invention is directed to the use of polyether antibiotics, e.g., monensin, dianemycin, A204, X206, nigericin and X537A as well as the pharmaceutically acceptable cationic salts and esters thereof in the treatment and prevention of swine dysentery. All the antibiotics and their salts are known and publications directed to their preparation are as follows:

Antibiotic X537A is a designation given to a crystalline antibiotic produced by a Streptomyces organism isolated from a sample of soil collected at Hyde Park, Mass. Lyophilized tubes of the culture bearing the laboratory designation X537 are deposited with the United States Department of Agriculture, Agricultural Research Service, Northern Utilization Research and Development Division, Peoria, Ill. The culture, given identification number NRRL 3382 and NRRL 3382R by the Agricultural Research Service, has been made available to the public through the NRRL.

Antibiotic X537A is prepared by growing the Streptomyces organism in an aerated submerged culture, with the pH of the broth adjusted to about neutral, i.e., about 6.5 to 7.5. The medium utilized contains a nitrogen source, such as yeast, a yeast derived product, corn meal, soy bean meal and the like, with soybean meal being the most preferred; and a carbohydrate source, such as beet, molasses, and the like, with brown sugar being the most preferred. The fermentation is carried out at slightly elevated temperatures, i.e., between about 25° and 35° C. with the preferred incubation temperature being about 28° C. After an incubation of 4 to 6 days, the fermentation broth is filtered and the antibiotic recovered by extraction.

Antibiotic X537A has a structural formula as given below:

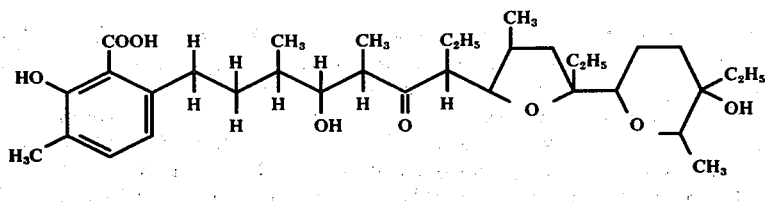

A detailed description of its preparation is found in Berger et al., J.A.C.S. 73, 5295–93 (1951). The compound is known to have activity as a coccidiostat agent and as an antibacterial agent.

Dianemycin has been characterized as having the following structural formula:

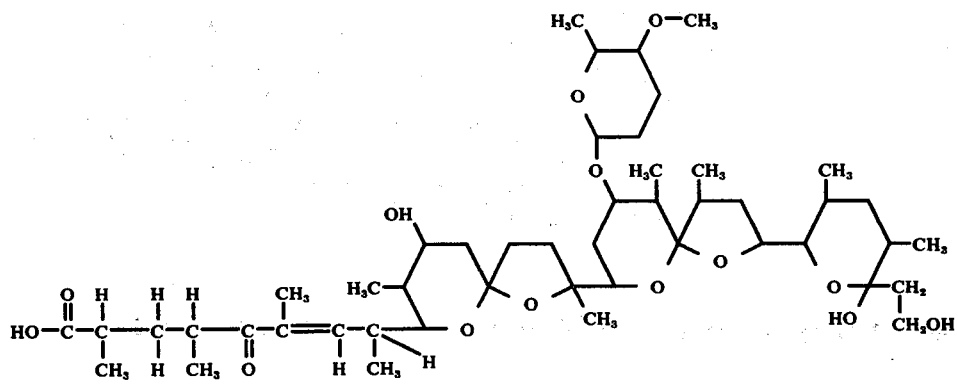

Steinrauf et al., Biochemical and Biophysical Research Communications 45, 1279–87 (1971).

Gorman et al., U.S. Pat. No. 3,577,531 gives the description, preparation and characteristics of dianemycin and refers to a previous article about it by Lardy et al., Arch. Biophysics 78, 587–97 (1958).

Dianemycin is a fermentation product of an organism which is a strain of Streptomyces hydroscopicus and is on an unrestricted deposit under the identification number NRRL 3444 in the Northern Utilization Research and Development Division, Agricultural Research Service, United States Department of Agriculture, Peoria, Ill.

Nigericin has been known for some time under the names helexin-C, antibiotic X464, antibiotic K178, polyetherin A, and azalomycin M. Its structure was characterized by Steinrauf et al., Biochemical and Biophysical Research Communications 33, 29 (1968). Its structural formula is depicted below:

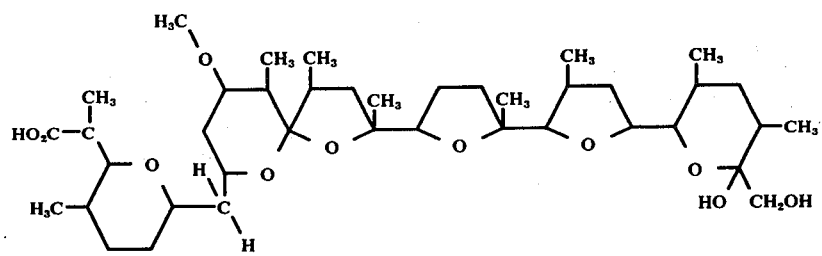

Harnes et al., Antibiotics and Chemotherapy I, 594–96 (1951) originally mentioned nigericin. It was also described by Gorman et al., U.S. Pat. No. 3,555,510.

The organism which produces nigericin is a strain of *Streptomyces violaceoniger* which is on unrestricted deposit under the identification number NRRL B1356 in the Northern Research and Utilization Development Division, Agricultural Research Service, United States Department of Agriculture, Peoria, Ill. The preparation of nigericin is described in U.S. Pat. No. 3,794,732.

Monensin was described by Haney et al., U.S. Pat. No. 3,501,568. The substance known as monensin is actually a mixture of four components. These four components are included in the term "monensin" as used herein. The structural formula indicated below is According to U.S. Pat. No. 3,797,732, the organism capable of producing antibiotic A204 has been placed on permanent deposit, without restriction, with the culture collection of the Northern Utilization Research and Development Division, Agricultural Research Service, U.S. Department of Agriculture, Peoria, Ill. and is available to the public under culture number NRRL 3384.

Component I of A204 is the most important and the most abundant. Component II constitutes about 5% of the mixture of A204 components produced. The other components are obtained in smaller quantities. The components of A204 are included in the term "Antibiotic A204". The structural formula indicated below is that of the acid form of A204 I.

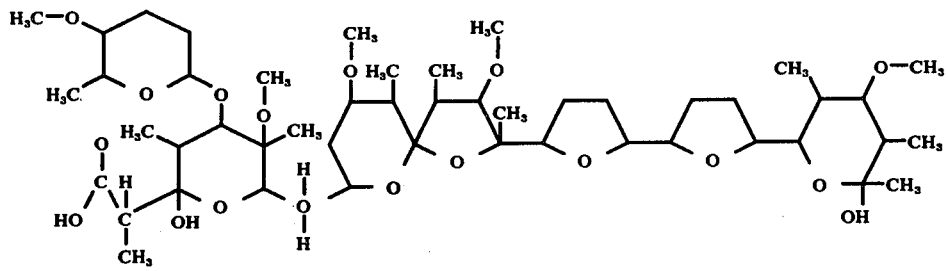

the acid form of the component A of monensin.

The antibiotic X206 was reported for the first time in

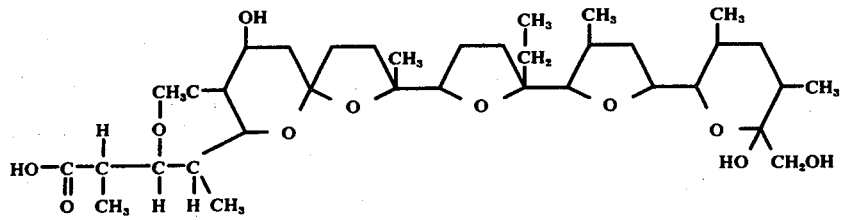

Monensin is the fermentation product of an organism which can be found on unrestricted deposit under the number ATCC 15413 in the American Type Culture Collection, Rockville, Md.

The antibiotic A204 is described and its preparation shown in U.S. Pat. No. 3,797,732. The term A204 is used to designate the different components obtained by fermentation in the presence of *Streptomyces albus* under aerobic conditions in a culture medium containing assimilable sources of carbon, nitrogen and inorganic salts. The organisms were first isolated from soil samples obtained from Perry, Fla.

1951 by Berger et al., JACS 73, 5295–98 (1951). The Streptomyces organism from which one is able to obtain antibiotic X206 is available at Center International d'Information sur Les Antibiotiques (International Center for Information on Antibiotics) Liege, Belgium, which lists the organism on page 31 of its Bulletin No. 3 (1966). X206 is characterized as being a molecule being very similar to those of other antibiotic compounds useful in the present process. Its formula has been depicted by Blount et al., Chemical Communication, 1971, 927–928 as follows:

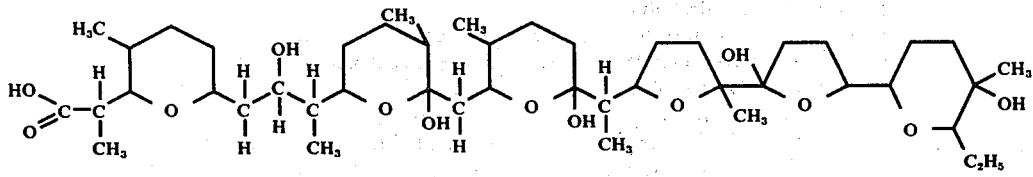

A method for the preparation of X206 is shown in U.S. Pat. No. 3,794,732.

The antibiotics which may be used in the present invention are all acids and react with organic and inorganic bases to form salts. Examples of mineral bases forming pharmaceutically acceptable cationic salts with the antibiotics include the alkaline metal hydroxides such as lithium hydroxide, sodium hydroxide and potassium hydroxide; the carbonates and the bicarbonates of alkaline metals such as lithium carbonate and sodium bicarbonate; hydroxides and carbonates of alkaline earth metals such as calcium hydroxide, magnesium carbonates; and similar mineral bases.

As examples of organic bases forming pharmaceutically acceptable salts with the antibiotics are lower alkyl amines, primary, secondary and tertiary hydroxy lower alkyl amines such as ethylamine, isopropylamine, diethylamine, methyl-n-butylamine, ethanolamine and diethanolamine. The ammonium salts of the antibiotics are prepared with ammonia or ammonium hydroxide.

The pharmaceutically acceptable esters of the acid group of antibiotics are obtained easily. For example, the alkyl esters such as methyl, isopropyl and butyl esters, cycloalkyl esters such as cyclopropyl and cyclohexyl esters, and aryl esters such as phenyl ester, can be obtained by reaction of the acid with a diazo derivative of the substituent to be added.

It is equally possible to obtain esters by acylation of one or more hydroxyl groups of these antibiotics. For example, esters are obtained by acylation with groups such as formyl, acetyl, hexanoyl and benzoyl groups or by a reaction with an anhydride of the acyl group to be added. The salts and esters of the antibiotics as described above are all useful in the process of this invention.

Swine dysentery is one of the most common swine diseases diagnosed in the United States. Additionally, the disease is prevalent in many other countries and annually causes many thousands of dollars losses in stock to swine growers around the world. It has recently been discovered that a large spirochete is the causative organism of the disease. This organism, *Treponema hyodysenteriae*, has now been isolated and shown to be capable of producing the disease [Harris, D. L. et al.: Swine Dysentery-1 Inoculation of Pigs with Treponema hyodysenteriae (New Species) and Reproduction of the Disease, Vet. Med/SAC 67: 61–64: 1972]. The test data recited hereinafter concerns tests conducted with this organism. It must be noted that it is not known whether *T. hyodysenteriae* is the sole causative organism of swine dysentery. From the data available, however, it can be concluded that it is a primary source of the infection.

The compounds described herein as being effective compounds in treating swine dysentery are all antibiotics with related structures. Each of the antibiotics has a chain of oxygenated rings with a single carboxylic acid group at one end of the molecule and one or more hydroxyl groups at the other end of the molecule.

All the active antibiotics in the present method form an unusual complex salt with a monovalent cationic metallic ion. A complex forms between one molecule of the antibiotic and one metallic ion. The atoms of oxygen to be found in the connected rings of the antibiotic molecule form a complex with a metallic ion. Thus, the antibiotic molecule forms a loop or ball around the ion. A weak covalent bond forms between the ion and each oxygen atom. The ends of the molecule are joined to each other by hydrogen bonds between the carboxyl group and a hydroxyl group located at the opposite end of the antibiotic molecule. Thus, the ion is completely enclosed in the antibiotic molecule. The unusual result is that the metallic salt of the antibiotic is insoluble in water but is soluble in the organic solvents. The compounds also form salts with other cations such as ammonium salts and amine salts.

It is expected that other antibiotics having the structures and general properties which have just been described could be used in the present method. These compounds clearly fall within the intended scope of the present invention.

The active ingredients and their pharmaceutically acceptable salts or esters have been found to control swine dysentery when administered to provide the active compound at levels as low as 0.0055% by weight of the feed ration. For effective prevention of swine dysentery, the active compounds or their pharmaceutically acceptable esters and salts can be administered at levels from about 0.0027% by weight to about 0.055% by weight preferably at about 0.015% by weight of the diet, and in the case of monensin, about 0.008% by weight of the diet for prevention and from about 0.0055% to about 0.0066% for control, i.e., 34 to 60 gms/ton.

For control and prevention of swine dysentery, it is preferred, in accordance with the present invention, to administer the antibiotic in feed ration. Therefore, the preferred method comprises administering to swine ad libitum a ration containing from about 0.0027% by weight to about 0.05% by weight active compound free acid or equivalent amount of a pharmaceutically acceptable salt or ester thereof.

As used herein "control" refers to treatment of infected animals and "prevention" refers to treatment of uninfected susceptible animals. Usually, less concentration of active compound is needed to achieve prevention than control since less severe conditions exist.

When in accordance with the invention the active compound is to be administered to swine in the form of an intimate admixture with a commercial dry feed ration, a premix or feed supplement is likewise contemplated. Such a premix can advantageously contain from about 1% by weight to about 99% by weight active compound or equivalent amount of a salt or ester thereof. Additionally, such a premix or feed supplement can contain inert carriers or diluents such as, for example, processed grain by products such as soybean mill runs and ground rice hulls, inorganic carriers such as oyster shell flour, anticaking agents such as calcium silicate and the like and may additionally contain compatible medicaments. A suitable premix can likewise be prepared by simply adding the desired concentration of active compound to a measured quantity of any commercial swine feed. A preferred premix is obtained using processed grain by-products. Such a premix can be added to commercial feed and intimately mixed therewith to effect uniform distribution thereby assuring an effective concentration level of active compound. The feed supplement or premix containing the active compound can be readily mixed with swine rations by any conventional technique for mixing feed. For convenience in commercial use, it has been found that premixes containing from about 1% by weight to about 80% by weight active compound are preferred, with a premix containing about 15% by weight being most preferred.

The following examples illustrate the invention.

EXAMPLE 1

This example illustrates typical feed supplement formulations suitable for use in the method of the invention. A premix is made from the following:

| Ingredient | Grams/Kilogram |
|---|---|
| Active Compound | 150.0 |
| Calcium Silicate (Microcel E) | 20.0 |
| Calcium Carbonate (Oyster Shell Flour) | 830.0 |
| Total Weight | 1000 gms. |

Procedure

The active compound is blended with Microcel E to make a pre-mix. The oyster shell flour is placed in a suitable mixer, the pre-mixer is added and the entire amount is mixed until homogeneous.

This premix is then added to commercial swine ration at the rate of 2 lb./ton to yield a concentration of about 136 gm./ton. The commercial feeds to which this premix is added may be free of other medicaments or may contain other medicaments if the final mixture is compatible therewith.

A premix is made from the following:

| Ingredient | Grams/Kilogram |
|---|---|
| Active Compound | 150.0 |
| Calcium Silicate (Microcel E) | 20.0 |
| Soy Oil | 20.0 |
| Soy Meal Run (toasted, extracted, milled soy) | 800.0 |
| Total Weight | 1000 gms. |
| Active Compound | 150.0 |
| Calcium Silicate (Microcel E) | 10.0 |
| Soy Oil | 20.0 |
| Ground Rice Hulls | 820.0 |
| Total Weight | 1000 gms. |

Procedure

The soy meal run or ground rice hulls is placed in a suitable mixer and about 20 grams (2% by weight of final mixture) of the soy oil slowly added thereto and the whole thoroughly mixed. The quantity of soybean (soy) oil is just sufficient to make the premix non-dusty and to prevent classification of the active compound and may be varied from lot to lot. The active ingredient with Microcel E is then added thereto and the whole thoroughly mixed until homogeneous.

These premixes are then combined with commercial feed formulations at the rate of 2 pounds per ton to yield final levels of active compound of 136 grams/ton.

EXAMPLE 2

Inoculum for 12 pigs to be designated as carrier pigs was obtained as follows: An original pure strain of Treponema hyodysenteriae (strain B-224) was isolated from an outbreak of swine dysentery in Illinois and passed twice in isolation units in pigs from a specific pathogen free herd or a disease controlled herd. Crude inoculum from the second passage was utilized to inoculate pigs in isolation from the disease controlled herd. Two of these pigs exhibiting mucohemorrhagic enteritis typical of swine dysentery were sacrificed. Intestinal scrapings of the colon and caecum were collected and diluted one to one with PBS, i.e., phosphate buffer solution. A sample of this material was found to be free of Salmonella spp. and to contain large numbers of the large spirochete T. hyodysenteriae which was isolated in pure culture.

Within 4 hours of collection, the buffered suspension of intestinal scrapings was used to inoculate 12 pigs designated hereafter as carrier pigs with 20 cc per os. Six days later, signs of swine dysentery began to appear in the carrier pigs. Ten days after inoculation, the surviving 10 carrier pigs (two had died of swine dysentery) were sacrificed. Two of these had only mild lesions of swine dysentery and were discarded. From the remaining pigs, colon contents and mucosal scrapings were pooled, diluted with PBS, and 20 ml. of this inoculum was administered per os to each of 48 experimental pigs. The experimental pigs were placed in 12 pens, each holding 4 pigs and fed non-medicated ration for five days. At that time, the rations containing from 0 to 136 grams/ton of active ingredient were fed ad libitum for 28 days after which non-medicated basal ration was fed 11 days to all pigs and the experiment was terminated. Each day, the number of pigs with diarrhea and hemorrhagic enteritis was noted. Pigs which died were necropsied and lesions of swine dysentery noted.

TABLE

| Summary of Effect of Dietary Antibiotic X-537A for Control of Swine Dysentery | | | | |
|---|---|---|---|---|
| | Group A | Group B | Group C | Group D |
| Antibiotic X-537A in ration, g/ton | 0 | 34 | 68 | 136 |
| Avg. daily intake, mg./lb. | 0 | 0.7 | 1.6 | 3.7 |
| Pigs started | 12 | 12 | 12 | 12 |
| Losses, mortality (+ culls) | 5(1) | 3 | 1(2) | 2 |
| Avg. diarrhea days per pen, experiment days 1–28[a]: | | | | |
| Diarrhea days | 81 | 61 | 56 | 66 |
| Hemorrhagic diarrhea days | 63 | 32 | 30 | 26 |
| Avg. diarrhea days per pen, | | | | |

TABLE-continued

Summary of Effect of Dietary Antibiotic X-537A for Control of Swine Dysentery

|  | Group A | Group B | Group C | Group D |
|---|---|---|---|---|
| experiment days 20-39[b]: |  |  |  |  |
| Diarrhea days | 30 | 18 | 21 | 11 |
| Hemorrhagic diarrhea days | 24 | 13 | 7 | 10 |
| Avg. pig weight, lb. |  |  |  |  |
| Initial (all pigs) | 45.1 | 43.2 | 43.2 | 45.0 |
| Initial (survivors) | 47.4 | 46.6 | 43.1 | 45.7 |
| Survivors after 28 days | 71.3 | 75.2 | 67.3 | 77.9 |
| Avg. daily gain, days 1-28 | 0.85 | 1.02 | 0.87 | 1.15 |
| Feed efficiency, days 1-28[c] | 0.289 | 0.364 | 0.332 | 0.350 |
| Avg. daily feed, days 1-28[c] | 2.88 | 2.67 | 2.61 | 3.33 |

[a]Of a total of 112 pig days (4 pigs/pen × 28 days). Corrected for mortality due to swine dysentery (SD).
[b]Of a total of 44 pig days (4 pigs/pen × 11 days). Corrected for SD mortality.
[c]Corrected for mortality.

The results above clearly indicate that the feeding ad libitum of a feed formulation containing about 34 to about 136 grams/ton active compound is highly efficacious in the control of swine dysentery and a feed containing about 136 grams per ton in efficacious in the majority of cases.

EXAMPLE 3

Swine dysentery was reproduced in your pigs by inoculating individual pigs with the spiral colon of seeder pigs. The inoculum contained *Treponema hyodysenteriae*-like spirochetes. The disease was monitored by following the clinical signs, necropsy lesions, fecal moisture quantitations, negative fecal Salmonella cultures and microscopic demonstration of T. hyodysenteriae-like spirochetes in the feces. The treatment was by allowing the pigs to eat medicated feed ad libitum. The results are shown in the following Table:

TABLE A

| Treatment | Concentration | Daily Dose mg/kg | No. of Days Treated | Results |
|---|---|---|---|---|
| Infected Untreated Control | — | 0 | 0 | 2/2 died, on day 3 and on day 9 |
| Monensin | .0088% (80 gm/ton) | 10 | 5 | 1/1 fair response |
|  | .0088% | 10 | 5 | 2/2 good response |

Fair response - diarrhea controlled after day 5 or 6 and remains normal.
Good response - feces normal after day 2 or 3 and remains normal.

The results indicate that monensin is active for controlling swine dysentery when used at the rate of about 10 mg/kg/day which is about 0.0088% by weight in feed or drinking water.

I claim:

1. A method for the prevention of swine dysentery which comprises orally administering ad libitum to swine susceptible to swine dysentery a ration containing from about 0.0027% by weight to about 0.055% by weight of, as the active compound, a polyether antibiotic selected from monensin, or equivalent amount of a pharmaceutically acceptable salt or ester thereof.

2. The method according to claim 1 wherein said antibiotic is monensin present in a concentration of 0.0088% by weight.

3. A method for the control of swine dysentery which comprises orally administering ad libitum to swine infected with swine dysentery a ration containing from about 0.0055% by weight to about 0.055% by weight of, as the active compound, a polyether antibiotic selected from monensin, or equivalent amount of a pharmaceutically acceptable salt or ester thereof.

4. The method according to claim 3 wherein said antibiotic is monensin.

5. The method of claim 4 wherein the ration contains from about 34 to about 60 grams/ton of said monensin or equivalent amount of a pharmaceutically acceptable salt or ester thereof.

* * * * *